US012708329B2

(12) United States Patent
Liu et al.

(10) Patent No.: US 12,708,329 B2
(45) Date of Patent: Aug. 18, 2026

(54) OPTICAL FILM FOR OXYGEN SATURATION SENSING

(71) Applicant: 3M INNOVATIVE PROPERTIES COMPANY, St. Paul, MN (US)

(72) Inventors: Zhiping Liu, Guangzhou (CN); Fan Long, Guangzhou (CN); John A. Wheatley, Stillwater, MN (US); Bharat R. Acharya, Woodbury, MN (US); Ryan T. Fabick, Shoreview, MN (US); Zhe Hu, Suzhou City (CN); Edward J. Kivel, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 459 days.

(21) Appl. No.: 18/266,049

(22) PCT Filed: Dec. 15, 2021

(86) PCT No.: PCT/IB2021/061780
§ 371 (c)(1),
(2) Date: Jun. 8, 2023

(87) PCT Pub. No.: WO2022/130247
PCT Pub. Date: Jun. 23, 2022

(65) Prior Publication Data

US 2024/0023905 A1 Jan. 25, 2024

Related U.S. Application Data

(60) Provisional application No. 63/126,018, filed on Dec. 16, 2020.

(51) Int. Cl.
*A61B 5/117* (2016.01)
*A61B 5/00* (2006.01)
*A61B 5/1455* (2006.01)

(52) U.S. Cl.
CPC .......... *A61B 5/7445* (2013.01); *A61B 5/0062* (2013.01); *A61B 5/117* (2013.01);
(Continued)

(58) Field of Classification Search
CPC .............. A61B 5/1455; A61B 5/14551; A61B 5/14552; A61B 5/7445; A61B 5/14558; A61B 5/6826
See application file for complete search history.

(56) References Cited

U.S. PATENT DOCUMENTS 6,024,455 A 2/2000 O'Neill et al.
7,972,266 B2 * 7/2011 Gobeyn ................ A61B 5/445 600/301

(Continued)

FOREIGN PATENT DOCUMENTS

KR 20170053019 A 5/2017
WO 2020053832 A1 3/2020

(Continued)

OTHER PUBLICATIONS

International Search Report for PCT International Application No. PCT/IB2021/061780, mailed on May 13, 2022, 6 pages.

(Continued)

*Primary Examiner* — Eric F Winakur
(74) *Attorney, Agent, or Firm* — Jonathan L. Tolstedt

(57) ABSTRACT

A display system for sensing a user body portion, including a display panel configured to form an image for viewing by the user, an optical reflector having a plurality of polymeric layers, and at least one optical sensor for sensing a visible light having at least one visible wavelength and an infrared light having at least one infrared wavelength. The optical sensor senses the visible and infrared lights after the visible and infrared lights are transmitted by the optical reflector. The optical reflector has an average optical reflectance greater than 80% in the visible wavelength range, an optical transmittance greater than about 50% at the infrared wavelength, an optical transmittance of greater than about 2% and less than about 10% at the visible wavelength, and an optical transmittance versus wavelength with a bandpass segment having a full width at half maximum that includes the visible wavelength.

12 Claims, 14 Drawing Sheets

(52) U.S. Cl.
CPC ...... *A61B 5/14552* (2013.01); *A61B 5/14558* (2013.01); *A61B 5/489* (2013.01); *A61B 5/6826* (2013.01)

(56) References Cited

U.S. PATENT DOCUMENTS

| | | | | |
|---|---|---|---|---|
| 9,301,694 | B2 * | 4/2016 | Gu | A61B 5/14551 |
| 10,750,982 | B2 | 8/2020 | Baek et al. | |
| 2010/0305418 | A1 * | 12/2010 | Deliwala | A61B 5/14551<br>600/324 |
| 2016/0238762 | A1 * | 8/2016 | Nevitt | G02B 5/0841 |
| 2018/0372932 | A1 * | 12/2018 | Kivel | G02B 5/26 |
| 2019/0290176 | A1 * | 9/2019 | Vu | A61B 5/14552 |
| 2020/0386931 | A1 * | 12/2020 | Johnson | G02B 5/0816 |

FOREIGN PATENT DOCUMENTS

| | | | |
|---|---|---|---|
| WO | 2022137060 | A1 | 6/2022 |
| WO | 2022248950 | A1 | 12/2022 |

OTHER PUBLICATIONS

Partial International Search for PCT International Application No. PCT/IB2021/061780, mailed on Mar. 22, 2022, 12 pages.

* cited by examiner

OPTICAL FILM FOR OXYGEN SATURATION SENSING

CROSS REFERENCE TO RELATED APPLICATIONS

This application is a national stage filing under 35 U.S.C. 371 of PCT/IB2021/061780, filed Dec. 15, 2021, which claims the benefit of U.S. Provisional Application No. 63/126,018, filed Dec. 16, 2020, the disclosures of which are incorporated by reference in their entireties herein.

SUMMARY

In some aspects of the present description, a display system for sensing a user body portion placed at or proximate to the display system is provided, including a display panel configured to form an image for viewing by the user, an optical reflector, and at least one optical sensor. The optical reflector includes a plurality of polymeric layers numbering at least 50 in total, and each of the polymeric layers has an average thickness of less than about 500 nm. The at least one optical sensor is configured to sense a visible light (i.e., human-visible) having at least one visible wavelength in a visible wavelength range extending from about 420 nm to about 680 nm, and an infrared light having at least one infrared wavelength in an infrared wavelength range extending from about 750 to about 1500 nm. The at least one optical sensor (e.g., may be two separate sensors) senses the visible and infrared lights after the visible and infrared lights are transmitted by the optical reflector. For a substantially normally incident light, the plurality of polymeric layers of the optical reflector has an average optical reflectance of greater than about 80% in the visible wavelength range, an optical transmittance of greater than about 50% at the at least one infrared wavelength, an optical transmittance of greater than about 2% and less than about 10% at the at least one visible wavelength, and an optical transmittance versus wavelength that includes a bandpass segment with a full width at half maximum (FWHM) that includes the at least one visible wavelength.

In some aspects of the present description, a display system is provided, including first and second optical reflectors. Each of the optical reflectors includes a plurality of polymeric layers numbering at least 50 in total, and each of the polymeric layers has an average thickness of less than about 500 nm. For a substantially normally incident light, at least one visible wavelength in a visible wavelength range extending from about 420 nm to about 680 nm, and at least one infrared wavelength in an infrared wavelength range extending from about 750 to about 1500 nm: the plurality of polymeric layers of each of the optical reflectors has an average optical reflectance of greater than about 80% in the visible wavelength range, and an optical transmittance of greater than about 2% at the at least one visible wavelength. For the substantially normally incident light, at least one visible wavelength, and the at least one infrared wavelength: the plurality of polymeric layers of the first optical reflector has an optical transmittance of greater than about 50% at the at least one infrared wavelength, and the plurality of polymeric layers of the second optical reflector has an optical reflectance of greater than about 50% at the at least one infrared wavelength.

DETAILED DESCRIPTION

Figure 1:
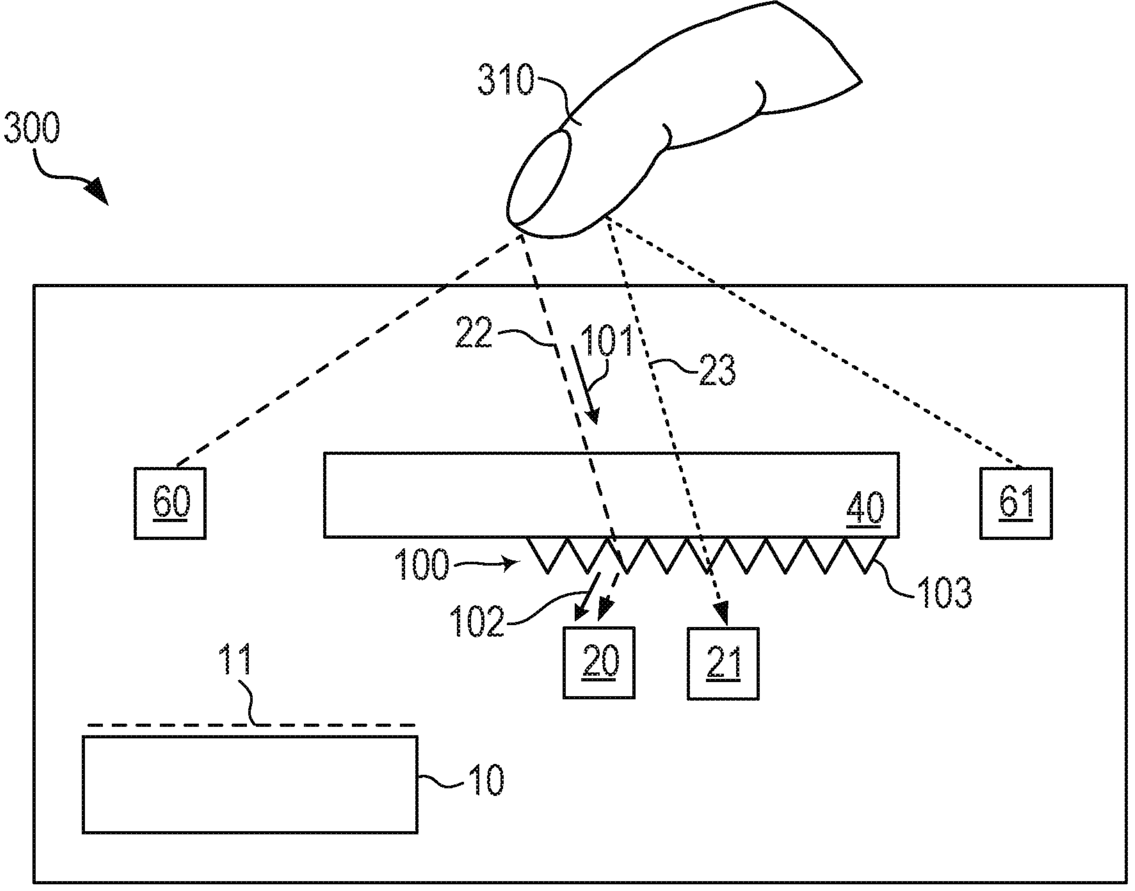
FIG. 1 is a schematic diagram of a display system for sensing a body portion of a user, in accordance with an embodiment of the present description.

In the following description, reference is made to the accompanying drawings that form a part hereof and in which various embodiments are shown by way of illustration. The drawings are not necessarily to scale. It is to be understood that other embodiments are contemplated and may be made without departing from the scope or spirit of the present description. The following detailed description, therefore, is not to be taken in a limiting sense.

An increasing number of portable electronic devices (e.g., smart phones, smart watches, laptops, etc.) are incorporating biometric authentication (e.g., fingerprint sensing) as part of their security and identification features. This trend is continuing, and there is a desire to expand functionalities in consumer electronic devices health monitoring beyond simple fingerprint sensing. For example, a user's oxygen saturation (SpO2) level has become a key metric in monitoring the health of a person (e.g., detecting low blood oxygen levels in potential COVID-19 patients). An increasing number of smart watches (e.g., Apple Series 6, Huawei GT2, etc.) have begun to support SpO2 measurement. In the past, some smart phone original equipment manufacturers have used rear cameras and infrared cameras to measure SpO2 levels, but this can be inconvenient and if often not accurate.

According to some aspects of the present description, an optical reflector film creates a small bandpass transmission of a at least one key wavelength for use in SpO2 detection (e.g., 660 nm) and controls the angle of light transmitted through a display system in order to enable SpO2 detection in a display system. A display system for sensing a user body portion placed at or proximate to the display system includes a display panel configured to form an image for viewing by the user, an optical reflector, and at least one optical sensor. In some embodiments, the optical reflector may include a plurality of polymeric layers numbering at least 50, or at least 100, or at least 250, or at least 300, or at least 400, or at least 500, or at least 600, in total. In some embodiments, each of the polymeric layers may have an average thickness of less than about 500 nm, or less than about 400 nm, or less than about 300 nm, or less than about 200 nm. In some embodiments, the optical reflector may further include at least one skin (e.g., an outer layer of the multilayer optical film) having an average thickness of greater than about 500, or greater than about 750, or greater than about 1000 nm.

The at least one optical sensor may be configured to sense a visible light having at least one visible wavelength (e.g., a wavelength of red light) in a visible wavelength range extending from about 420 nm to about 680 nm, and an infrared light having at least one infrared wavelength in an infrared wavelength range extending from about 750 to about 1500 nm. In some embodiments, the at least one optical sensor may sense the visible and infrared lights after the visible and infrared lights are transmitted by the optical reflector. In some embodiments, the at least one visible wavelength may include at least one of a green wavelength and a red wavelength. In some embodiments, the at least one visible wavelength comprises a red wavelength of about 660 nm. In some embodiments, the at least one infrared wavelength may include a wavelength at one or of a wavelength at about 850 nm, a wavelength at about 940 nm, a wavelength at about 1000 nm, a wavelength at about 1150, and a wavelength at about 1200 nm.

In some embodiments, for a substantially normally incident light, the plurality of polymeric layers of the optical reflector may have an average optical reflectance of greater than about 80%, or greater than about 85%, or greater than about 90%, or greater than about 95%, in the visible wavelength range, an optical transmittance of greater than about 50%, or greater than about 60%, or greater than about 65%, or greater than about 70%, or greater than about 75%, or greater than about 80%, at the at least one infrared wavelength, an optical transmittance of greater than about 2%, or greater than about 2.5%, or greater than about 3%, or greater than about 3.5%, or greater than about 4%, and less than about 10% at the at least one visible wavelength, and an optical transmittance versus wavelength that includes a bandpass segment including a full width at half maximum (FWHM) that includes the at least one visible wavelength. In some embodiments, the FWHM of the bandpass segment is less than about 200 nm, or less than about 150 nm, or less than about 125 nm, or less than about 100 nm, or less than about 80 nm, or less than about 70 nm, or less than about 60 nm, or less than about 50 nm, or less than about 40 nm, or less than about 30 nm, or less than about 20 nm wide. In some embodiments, the bandpass segment may include a global peak at a global peak wavelength disposed in the visible wavelength range. In some embodiments, the at least one visible wavelength is within about 50 nm, or about 40 nm, or about 30 nm, or about 20 nm of a global maximum of the bandpass segment.

In some embodiments, a polymer layer thickness gradient of the plurality of polymeric layers of the optical reflector includes first and second substantially linear portions joined by a third substantially linear portion, each of the first and second portions extending across at least 75, or at least 100, or at least 125, or at least 150, or at least 175, or at least 200, or at least 225, sequentially arranged polymeric layers in the plurality of polymeric layers, and the third linear portion extending across less than about 75 sequentially arranged polymeric layers in the plurality of polymeric layers. In some embodiments, best linear fits to each of the first, second, and third substantially linear portions may have respective linear slope magnitudes S1, S2 and S3, such that S3 is greater than each of S1 and S2 by at least a factor of 1.5, or at least a factor of 1.6, or at least a factor of 1.7, or at least a factor of 1.8, or at least a factor of 1.9, or at least a factor of 2.0, or at least a factor of 2.1, or at least a factor of 2.2.

In some embodiments, the display system may further be configured to image the user body portion. In some embodiments, the user body portion may include one or more of a finger of the user, a palm of the user, a vein of the user, a face of the user, and a vein pattern of the user. In some embodiments, the at least one optical sensor may be configured to at least measure an intensity of at least one of the visible and infrared lights, for the purpose of forming a one- or a two-dimensional image of the user body portion. In some embodiments, the at least one optical sensor may include a visible light optical detector configured to sense the visible light having the at least one visible wavelength, and an infrared light optical detector configured to sense the infrared light having the at least one infrared wavelength. In some embodiments, the display system may further include at least one light source configured to emit the visible light having the at least one visible wavelength and the infrared light having the at least one infrared wavelength, such that the emitted visible and infrared lights are sensed by the at least one optical sensor after the emitted visible and infrared lights are first reflected by the user body portion and then transmitted by the optical reflector. In some embodiments, the at least one light source may include a visible-light light source (60) configured to emit the visible light having the at least one visible wavelength and an infrared-light light source (61) configured to emit the infrared light having the at least one infrared wavelength.

In some embodiments, the optical reflector may be disposed between the display panel and the at least one optical sensor. In some embodiments, the display system may further include a light redirecting layer (e.g., a film including a plurality of prisms) disposed on the optical reflector for redirecting at least one of the visible and infrared lights from propagating along a first direction to a propagating along a different second direction. In some embodiments, where the optical reflector is disposed between the display panel and the at least one optical sensor, the display system may further include at least one light source configured to emit the visible light having the at least one visible wavelength and the infrared light having the at least one infrared wavelength, the optical reflector disposed between the display panel and the at least one light source, such that the emitted visible and infrared lights are sequentially transmitted by the optical reflector, transmitted by the display panel, reflected by the user body portion, transmitted by the display panel, transmitted by the optical reflector, and sensed by the at least one optical sensor. In such embodiments, the display system may further include a visible-light light source included in the display panel and configured to emit the visible light having the at least one visible wavelength and an infrared-light light source disposed between the display panel and the optical reflector. In such embodiments, the visible-light light source may also be configured to emit the infrared light having the at least one infrared wavelength, such that the emitted visible light is sequentially reflected by the user body portion, transmitted by the display panel, transmitted by the optical reflector, and sensed by the at least one optical sensor, and the emitted infrared light is sequentially transmitted by the display panel, reflected by the user body portion, transmitted by the display panel, transmitted by the optical reflector, and sensed by the at least one optical sensor.

In some embodiments of the display system, at least one of the at least one optical sensor is disposed between the optical reflector and the display panel. In such embodiments, the display system is configured to sense a user body portion (e.g., a finger) applied to a back side of the display system opposite the image formed by the display panel. In such embodiments, the display system may further include a cover disposed on the back side of the display system, and the optical reflector may be disposed between the cover and the at least one optical sensor, such that for a substantially normally incident light and for each of the at least one visible wavelength and the at least one infrared wavelength, the cover has an optical transmittance of greater than about 50%, or greater than about 60%, or greater than about 70%, or greater than about 80%. In such embodiments, the display system may further include at least one light source disposed between the optical reflector and the display panel, which is configured to emit the visible light having the at least one visible wavelength as well as the infrared light having the at least one infrared wavelength, such that the emitted visible and infrared lights are sequentially transmitted by the optical reflector, reflected by the user body portion, transmitted by the optical reflector, and sensed by the at least one optical sensor. In such embodiments, at least one light source may include a visible-light light source configured to emit the visible light having the at least one visible wavelength and an infrared-light light source configured to emit the infrared light having the at least one infrared wavelength. In such embodiments, the display system may also further include a display, the display including the display panel disposed between first and second polarizers. In such embodiments, at least one of the first and second polarizers may be or include an absorbing polarizer. In such embodiments, the display system may further include a visible-light light source disposed in the display and configured to emit the visible light having the at least one visible wavelength and an infrared-light light source disposed between the optical reflector and the display and configured to emit the infrared light having the at least one infrared wavelength.

In some such embodiments, the display may further include a second optical reflector disposed between the optical reflector and the display panel, such that for a substantially normally incident light, the second optical reflector has an average optical reflectance of greater than about 80%, or greater than about 90%, or greater than about 95%, in the visible wavelength range and an optical reflectance of greater than about 80%, or greater than about 90%, or greater than about 95%, at the at least one infrared wavelength. In such embodiments, the second optical reflector may include at least one first segment that has an optical transmittance of greater than about 5%, or greater than about 10%, or greater than about 20%, at the at least one visible wavelength. In such embodiments, the at least one first segment may include a physical through-opening in the second optical reflector. In such embodiments, the at least one optical sensor may include a visible light optical detector configured to sense the visible light having the at least one visible wavelength and disposed between the optical reflector and the display, or disposed on a lateral side of the display, and an infrared-light optical detector configured to sense the infrared light having the at least one infrared wavelength and disposed between the optical reflector and the display panel.

According to some aspects of the present description, a display system includes first and second optical reflectors. In some embodiments, each of the first and second optical reflectors includes a plurality of polymeric layers numbering at least 50, or at least 100, or at least 250, or at least 300, or at least 400, or at least 500, or at least 600, in total, each of the polymeric layers having an average thickness of less than about 500 nm, or less than about 400 nm, or less than about 300 nm, or less than about 200 nm. For a substantially normally incident light, at least one visible wavelength in a visible wavelength range extending from about 420 nm to about 680 nm, and at least one infrared wavelength in an infrared wavelength range extending from about 750 to about 1500 nm: the plurality of polymeric layers of each of the optical reflectors may have an average optical reflectance of greater than about 80%, or greater than about 85%, or greater than about 90%, or greater than about 95%, in the visible wavelength range, and an optical transmittance of greater than about 2%, or greater than about 2.5%, or greater than about 3%, or greater than about 3.5%, or greater than about 4%, or greater than about 10%, or greater than about 20%, or greater than about 30%, at the at least one visible wavelength. In some embodiments, the plurality of polymeric layers of the first optical reflector may have an optical transmittance of greater than about 50%, or greater than about 60%, or greater than about 65%, or greater than about 70%, or greater than about 75%, or greater than about 80%, at the at least one infrared wavelength. In some embodiments, the plurality of polymeric layers of the second optical reflector may have an optical reflectance of greater than about 50%, or greater than about 60%, or greater than about 65%, or greater than about 70%, or greater than about 75%, or greater than about 80%, at the at least one infrared wavelength.

Turning now to the drawings, FIG. 1 provides a schematic diagram of a display system for sensing a body portion of a user, according to the present description. In some embodiments, display system 300 for sensing a user body portion 310 (e.g., a finger of a user) at or proximate to the display system may include a display panel 10, an optical reflector 40, and at least one optical sensor 20, 21. In some embodiments, display panel 10 may be configured to form an image 11 for viewing by a user. In some embodiments, the at least one optical sensor 20, 21 may be configured to sense a visible light 22 having at least one visible wavelength in a human-visible wavelength range extending from about 420 nm to about 680 nm, and an infrared light 23 having at least one infrared wavelength in an infrared wavelength range extending from about 750 to about 1500 nm. In some embodiments, the at least one optical sensor 20, 21 may sense the visible light 22 and infrared light 23 after they are transmitted by optical reflector 40.

In some embodiments, user body portion 310 may be a finger of a user (as shown in FIG. 1), but may also be a palm of a user, a vein of a user, a vein pattern of a user, and a face of a user, or any other appropriate body portion. In some embodiments, user body portion 310 may be disposed under the skin of a user, such as a pattern of blood vessels beneath the skin of a user. In some embodiments, display system 300 may be further configured to capture an image of the user body portion. In some embodiments, the at least one optical sensor 20, 21 may be configured to at least measure an intensity of at least one of the visible light 22 and infrared light 23, and form a one-dimensional or two-dimensional image of the user body portion.

In some embodiments, display system 300 may further include at least one light source 60, 61 configured to emit the visible light 22 having the at least one visible wavelength and the infrared light 23 having the at least one infrared wavelength, such that the emitted visible light 22 and infrared light 23 are sensed by the at least one optical sensor 20, 21 after the emitted visible light 22 and infrared light 23 are first reflected by user body portion 310 and then transmitted by optical reflector 40.

In some embodiments, the at least one optical sensor 20, 21 may include a visible-light optical detector 20 configured to sense visible light 22 having the at least one visible wavelength, and an infrared-light optical detector 21 configured to sense the infrared light having the at least one infrared wavelength. In some embodiments, the at least one light source 60, 61 may include a visible-light light source 60 configured to emit the visible light having the at least one visible wavelength, and an infrared-light light source 61 configured to emit the infrared light having the at least one infrared wavelength.

In some embodiments, display system 300 may further include a light redirecting layer 100 disposed on at least a portion of optical reflector 40 for redirecting at least one of visible light 22 and infrared light 23 from propagating along a first direction 101 to propagating along a different second direction 102. In some embodiments, light redirecting layer 100 may include a plurality of prisms 103.

Figure 2:
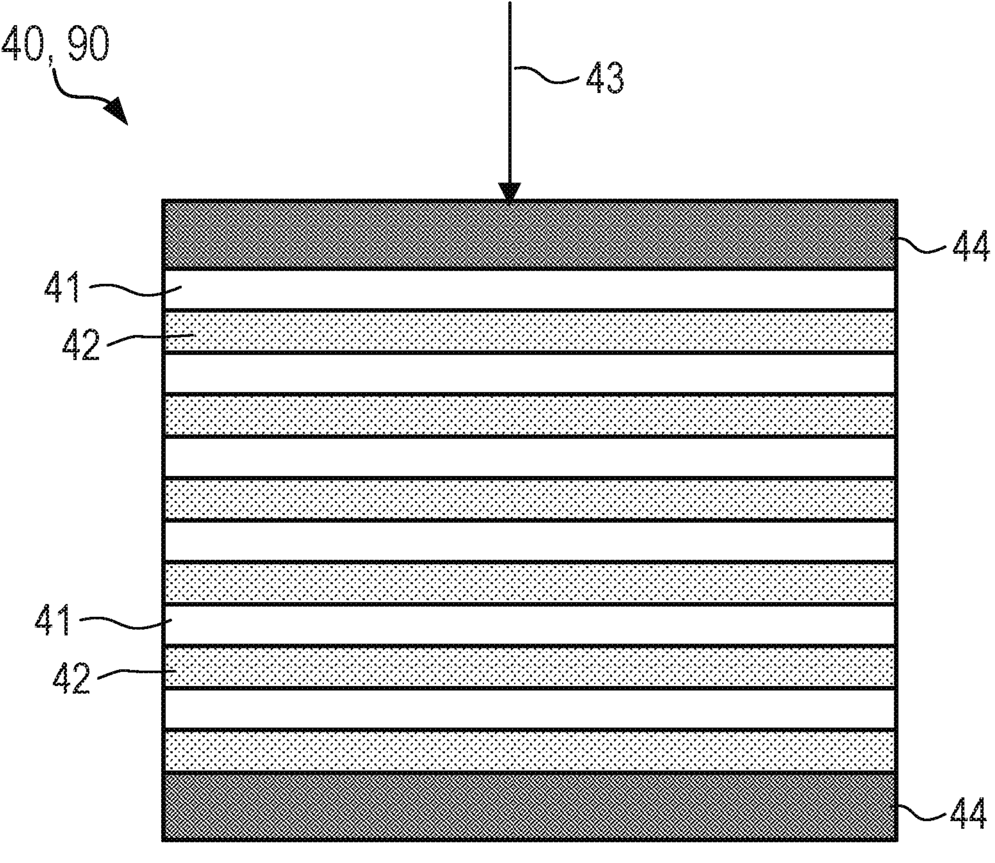
FIG. 2 is an illustration of an optical reflector with a plurality of polymeric layers, in accordance with an embodiment of the present description.

FIG. 2 is an illustration of the construction of an optical reflector, such as optical reflector 40 of FIG. 1. In some embodiments, optical reflector 40 (and, in some additional embodiments, optical reflector 90, to be discussed in FIG. 11) includes a plurality of alternating polymeric layers 41, 42 numbering least 50, or at least 100, or at least 250, or at least 300, or at least 400, or at least 500, or at least 600 in total. In some embodiments, each of polymeric layers 41, 42 may have an average thickness of less than about 500 nm, or about 400 nm, or about 300 nm, or about 200 nm. In some embodiments, optical reflector 40 may further include at least one skin 44 having an average thickness of greater than about 500, or greater than about 750, or greater than about 1000 nm. In some embodiments, optical reflector 40 may include skins 44 as opposing outermost layers, as shown in FIG. 2. In some embodiments, optical reflector 40 may, for a substantially normally incident light 43, exhibit certain desirable optical characteristics, as described elsewhere herein.

Figure 3:
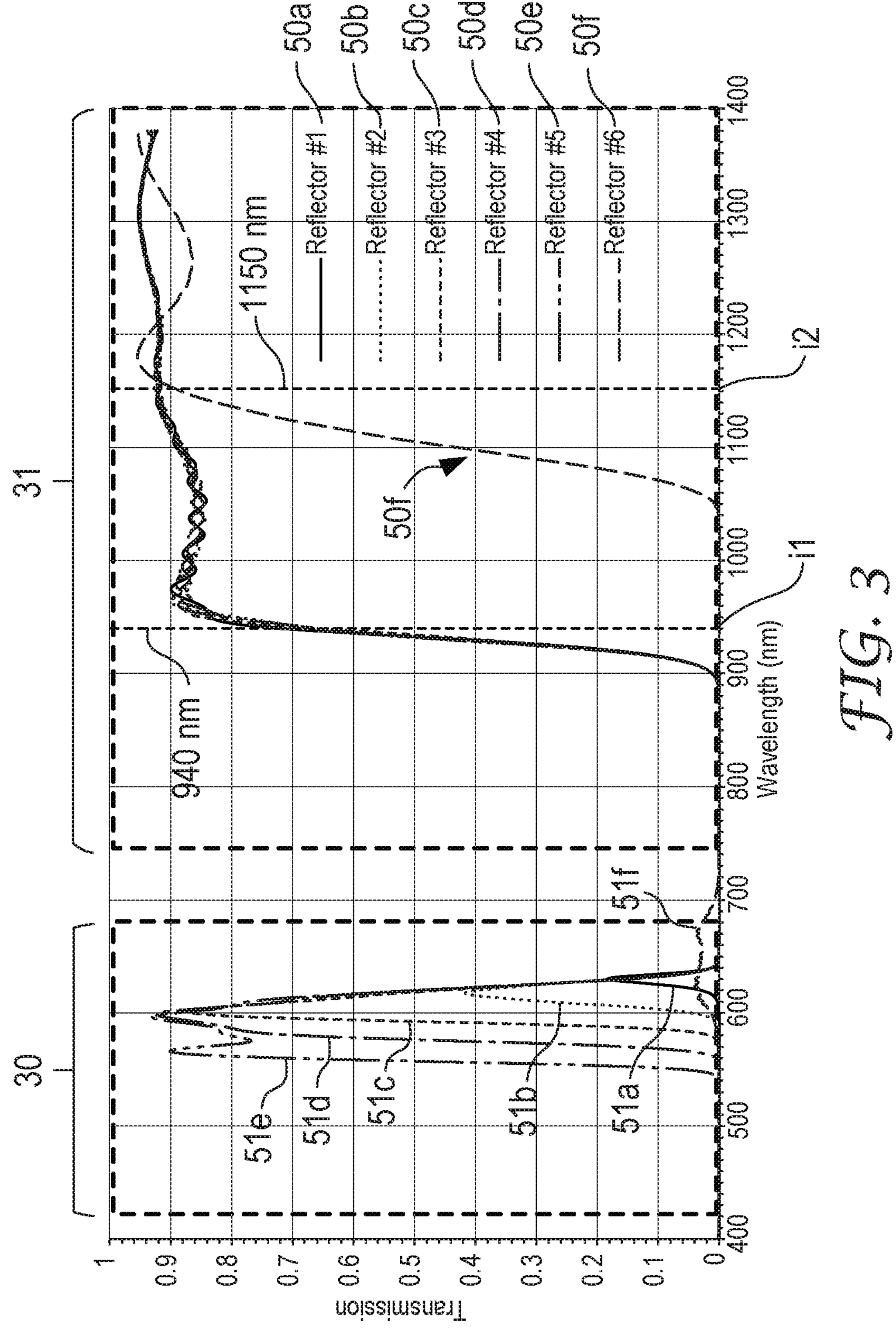
FIG. 3 is a plot of percent optical transmission versus wavelength for various layers of an optical stack for both visible and infrared wavelengths, in accordance with an embodiment of the present description.
Figure 4:
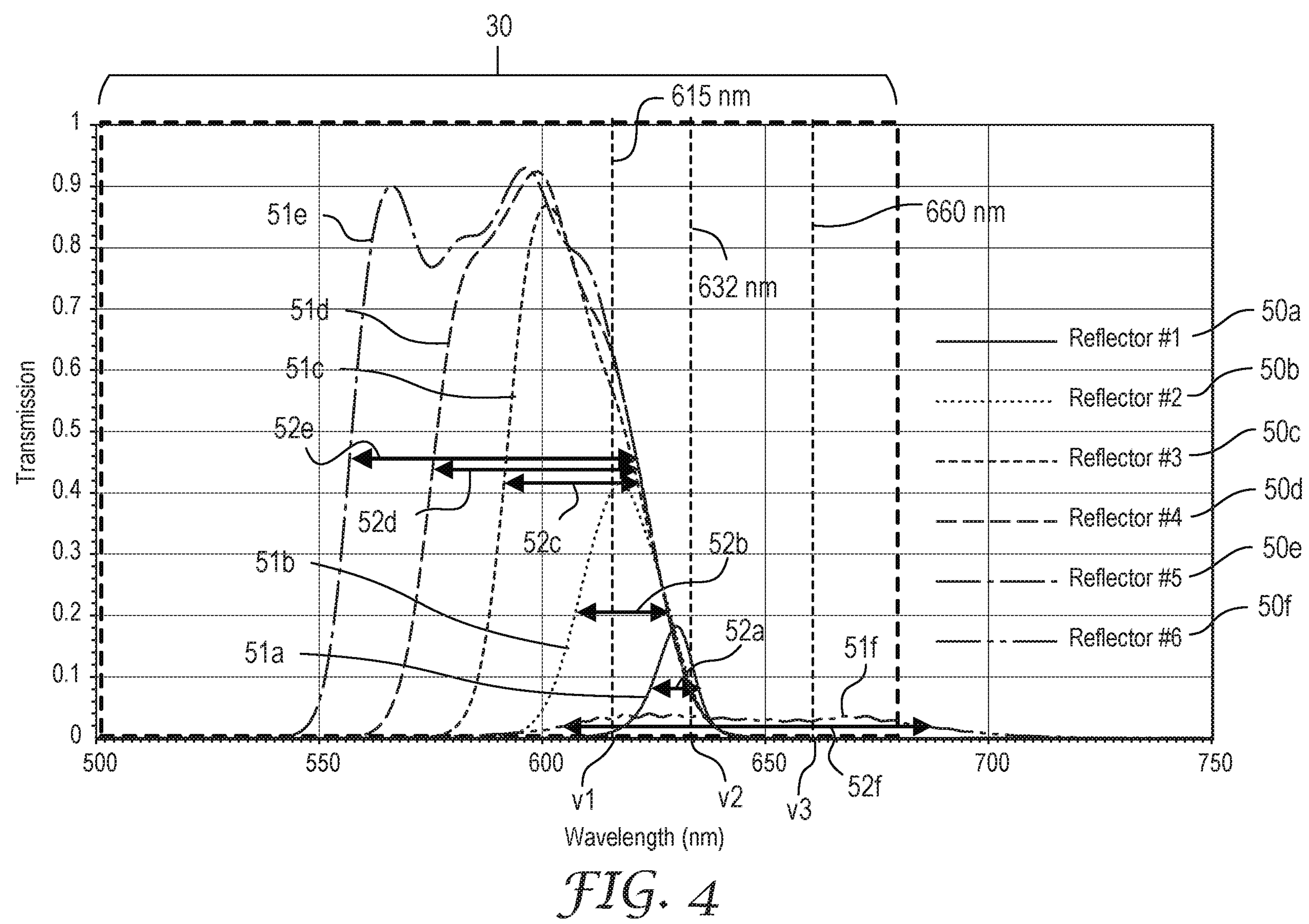
FIG. 4 is a plot of percent optical transmission versus wavelength for various layers of an optical stack for visible wavelengths, including full width at half maximum values for each plot, in accordance with an embodiment of the present description.

For example, FIGS. 3 through 7B provide plots of percent optical transmission versus wavelength for various reflector types which may be used in an optical stack. For the following discussion, two or more of FIGS. 3 through 7B may be referenced simultaneously. In addition, the components shown in FIG. 1 may be referenced during the following discussion. The at least one optical sensor 20, 21 of display system 300 (see at least FIG. 1) may, in some embodiments, be configured to sense visible light 22 having at least one visible wavelength v1, v2, v3 (as shown in FIG. 4) in visible wavelength range 30, extending from about 420 nm to about 680 nm, and at least one infrared wavelength i1, i2 (as shown in FIG. 3) in infrared wavelength range 31, extending from about 750 nm to about 1500 nm (for simplicity, FIG. 3 only extends to about 1400 nm, but the optical characteristics discussed herein extend up to at least about 1500 nm).

FIGS. 3 and 4 provide plots of various reflector types 50*a*, 50*b*, 50*c*, 50*d*, 50*e*, and 50*f*, including the percentage of optical transmission each exhibits over visible wavelength range 30 and infrared wavelength range 31. Each of plots 50*a*, 50*b*, 50*c*, 50*d*, 50*e*, and 50*f*, representing the plots of the various reflector types, may have a corresponding bandpass region 51*a*, 51*b*, 51*c*, 51*d*, 51*e*, and 51*f*, as well as an associated FWHM values 52*a*, 52*b*, 52*c*, 52*d*, 52*e*, and 52*f*. In some embodiments, the FWHM 52*a*-52*f* of the bandpass segments 51*a*-51*f* may be less than about 200 nm, or about 150 nm, or about 125 nm, or about 100 nm, or about 80 nm, or about 70 nm, or about 60 nm, or about 50 nm, or about 40 nm, or about 30 nm, or about 20 nm wide.

Of particular interest for the present discussion is plot 51*f*, representing the optical transmission curve for an embodiment of optical reflector 40 (optical reflector 40, FIG. 1). Looking at FIG. 3, for a substantially normally incident light 43 (light 43, FIG. 2), the plurality of polymeric layers 41, 42 of optical reflector 40 may have an average optical reflectance of greater than about 80%, or greater than about 85%, or greater than about 90%, or greater than about 95%, in the visible wavelength range (it should be noted that, as FIG. 3 is a plot of transmission percentage versus wavelength, and that optical reflectance can be determined by subtracting the transmission percentage from 100% at any given wavelength on the plot of FIG. 3. A plot of optical reflection percent versus wavelength in the visible wavelengths can also be found in FIGS. 7A and 7B). In addition, the plurality of polymeric layers 41, 42 of optical reflector 40 may have an optical transmittance of greater than about 2%, or greater than about 2.5%, or greater than about 3%, or greater than about 3.5%, or greater than about 4%, and less than about 10% at the at least one visible wavelength (for example, for visible wavelengths v1, v2, and v3 shown in FIG. 4). In some embodiments, the plurality of polymeric layers 41, 42 of optical reflector 40 may have an optical transmittance versus wavelength 50*f* that includes a bandpass segment 51*f* which includes a full width at half maximum (FWHM) (see FIG. 4, 52*f*) that includes the at least one visible wavelength v1, v2, v3. For example, wavelength v1 (about 615 nm), wavelength v2 (about 632 nm), and wavelength v3 (about 660 nm) fall within the FWHM 52*f* of bandpass region 51*f*. The amount of transmission allowed in bandpass region 51*f* may be low, as shown in FIGS. 3 and 4, allowing just enough transmission of a visible wavelength (e.g., v3) to be detected by visible-light optical detector 20 (FIG. 1), enabling SpO2 detection (for example). In some embodiments, at least one of the visible wavelengths v1, v2, v3 may include a green wavelength and/or a red wavelength.

In some embodiments, the plurality of polymeric layers 41, 42 of the first optical reflector 40 may also have an optical transmittance of greater than about 50%, or greater than about 60%, or greater than about 65%, or greater than about 70%, or greater than about 75%, or greater than about 80%, at the at least one infrared wavelength i1, i2. For example, as shown in FIG. 3, at least wavelength i2 (about 1150 nm) in infrared wavelength range 31 has an optical transmittance of about 88% through optical reflector 40 (plot 50*f*).

Figure 5:
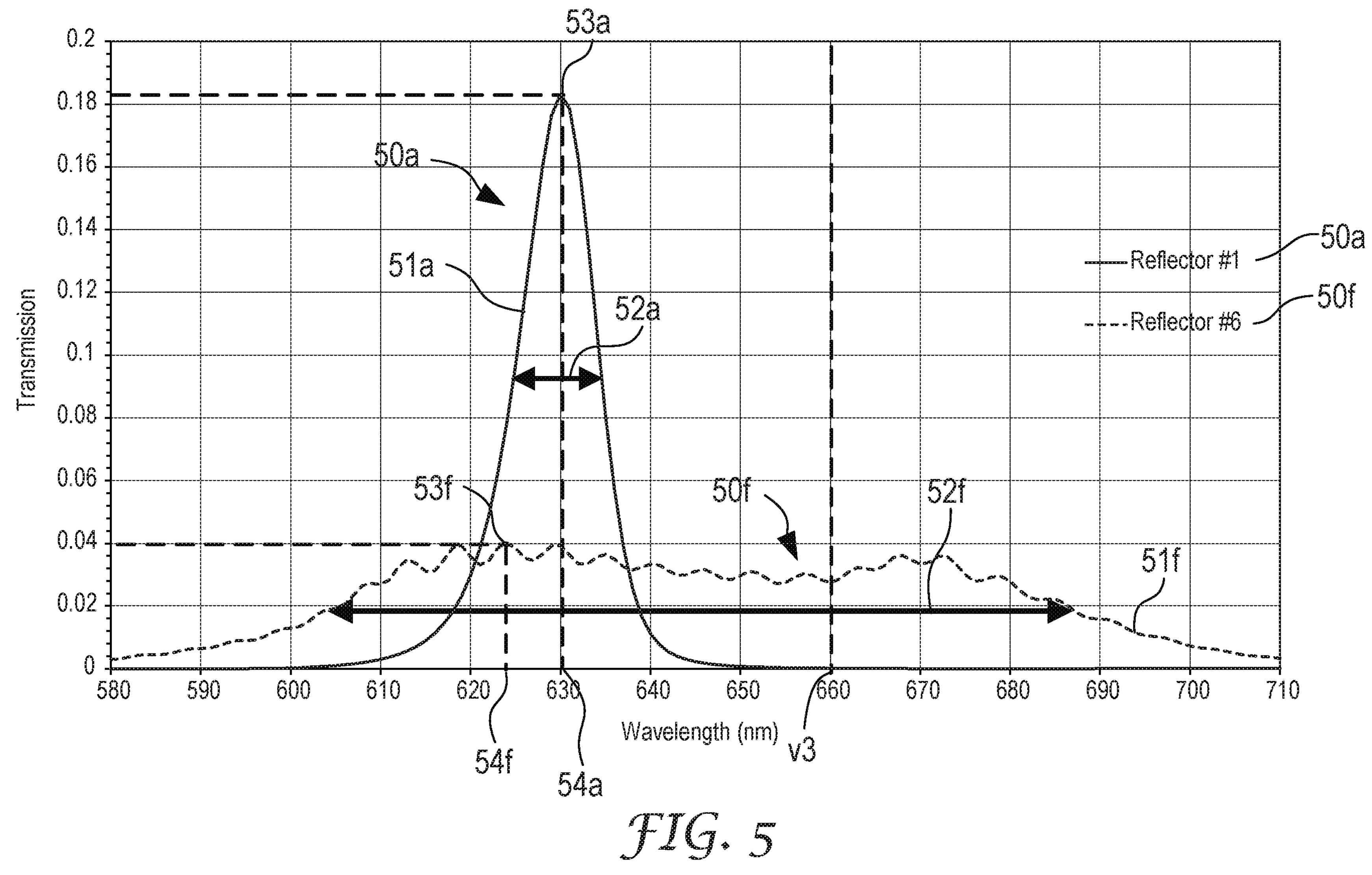
FIG. 5 is plot of percent optical transmission versus wavelength for various layers of an optical stack, showing additional details for a range of visible wavelengths, in accordance with an embodiment of the present description.
Figure 6A:
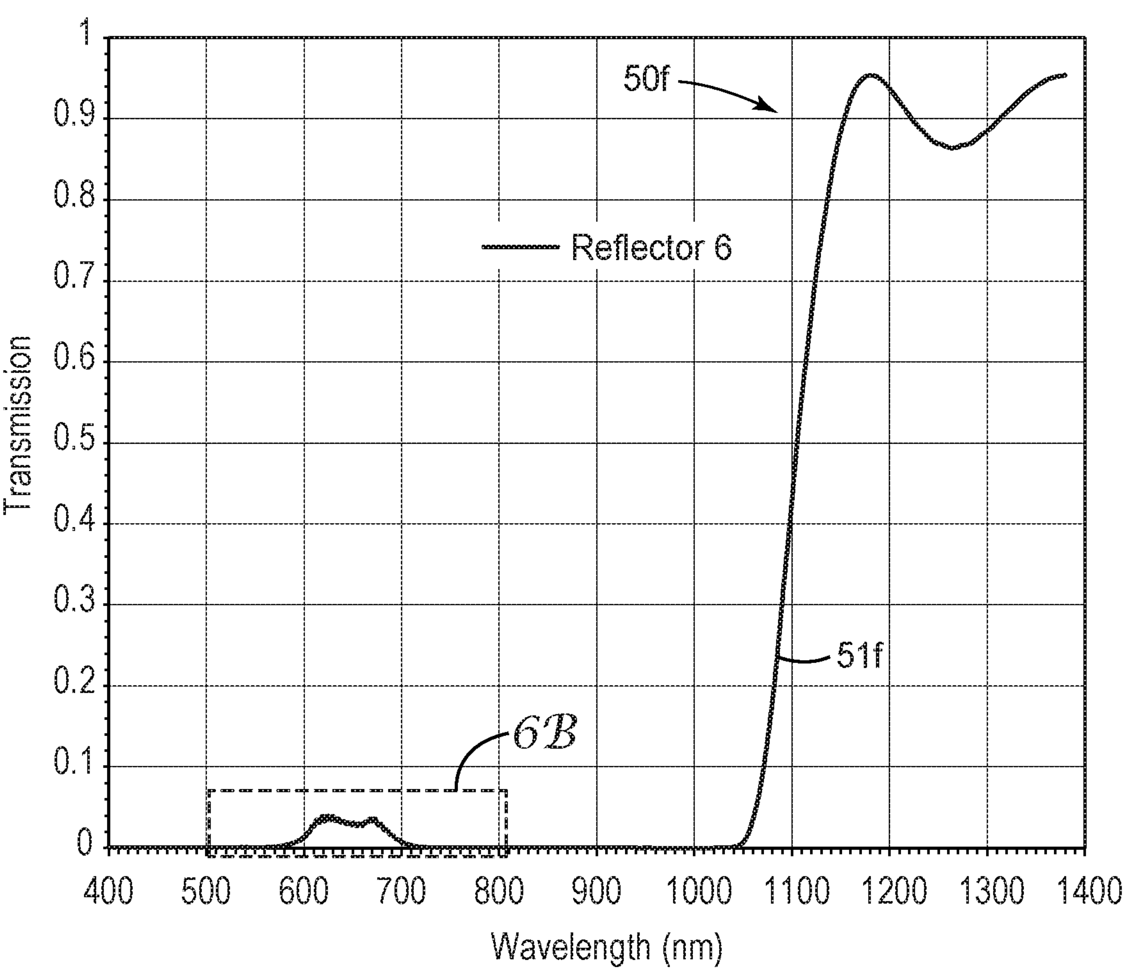
FIGS. 6A and 6B are plots of percent optical transmission versus wavelength for an optical reflector allowing a small bandpass transmission in the visible wavelengths, in accordance with an embodiment of the present description.
Figure 6B:
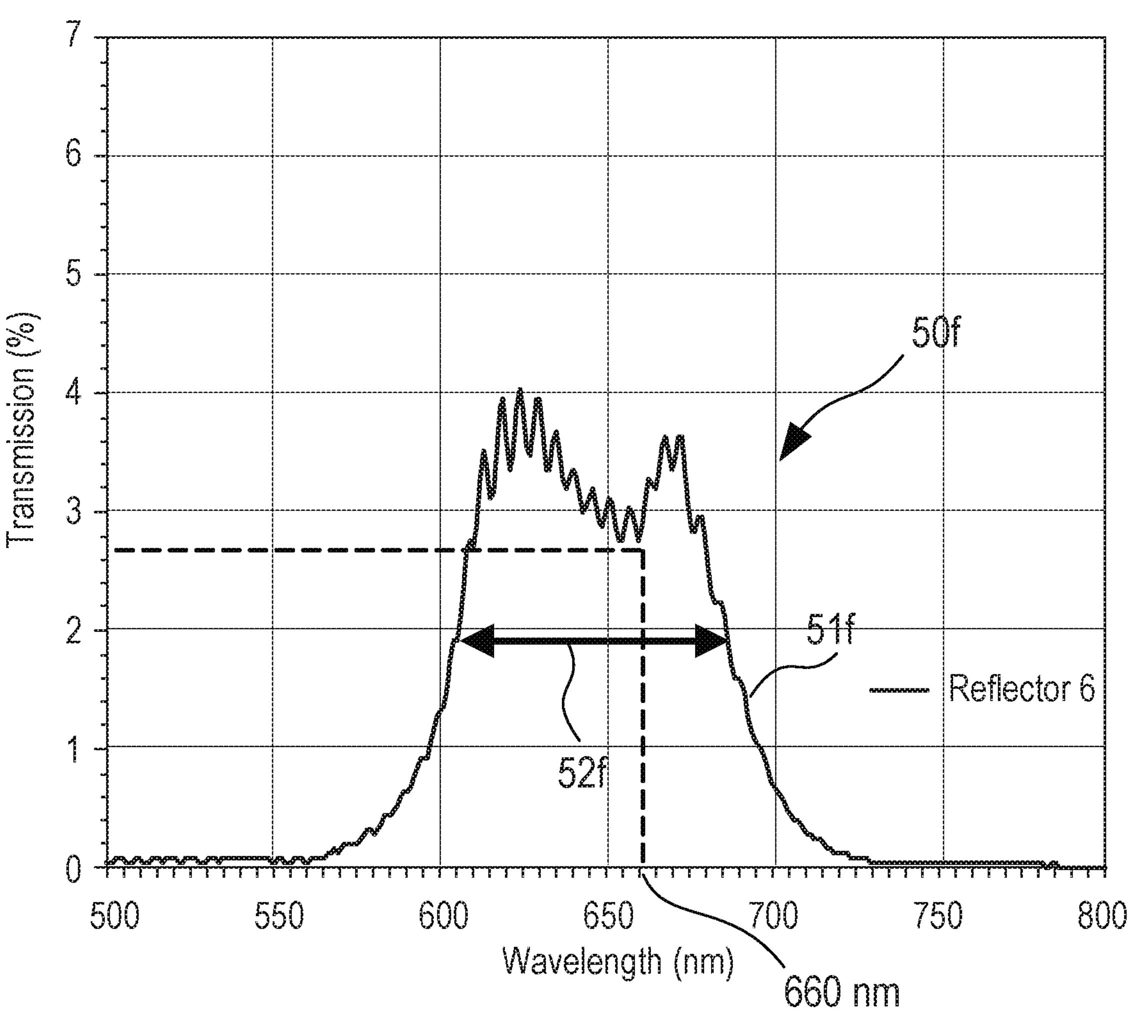
Figure 7A:
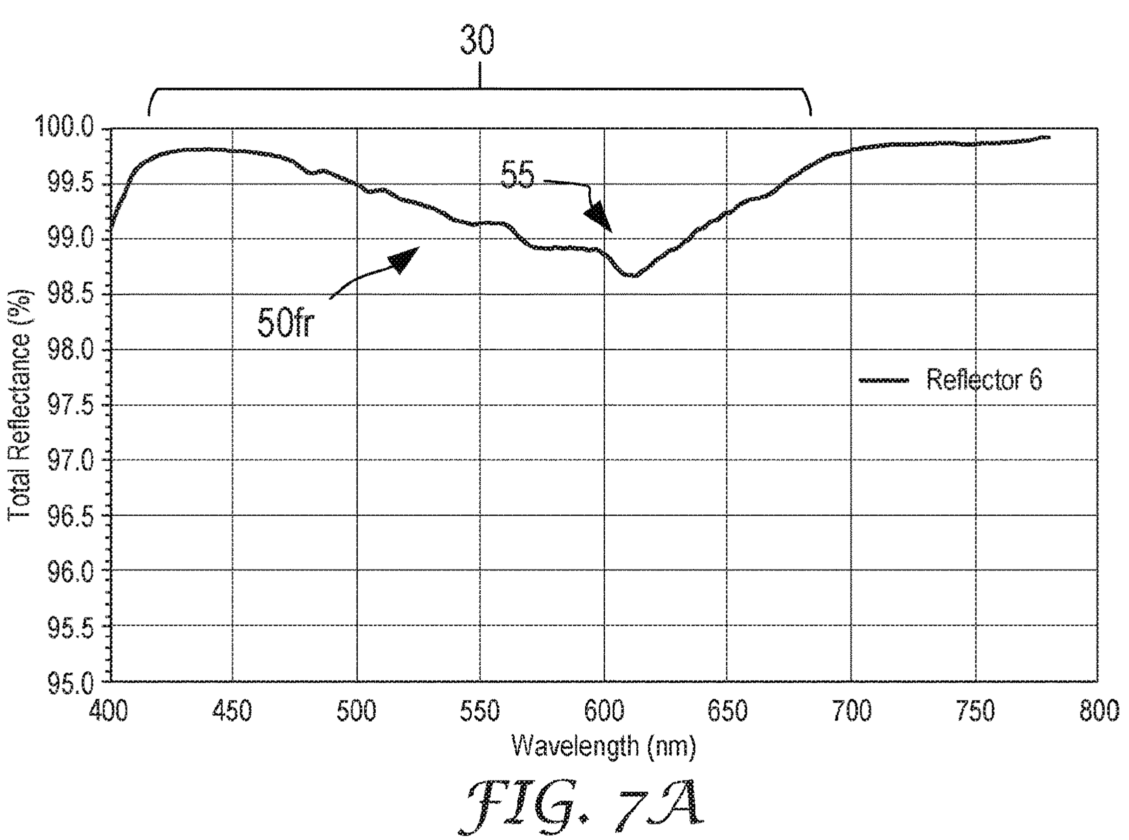
FIGS. 7A and 7B are plots of percent optical reflectance versus wavelength for an optical reflector in the visible wavelengths, in accordance with an embodiment of the present description.
Figure 7B:
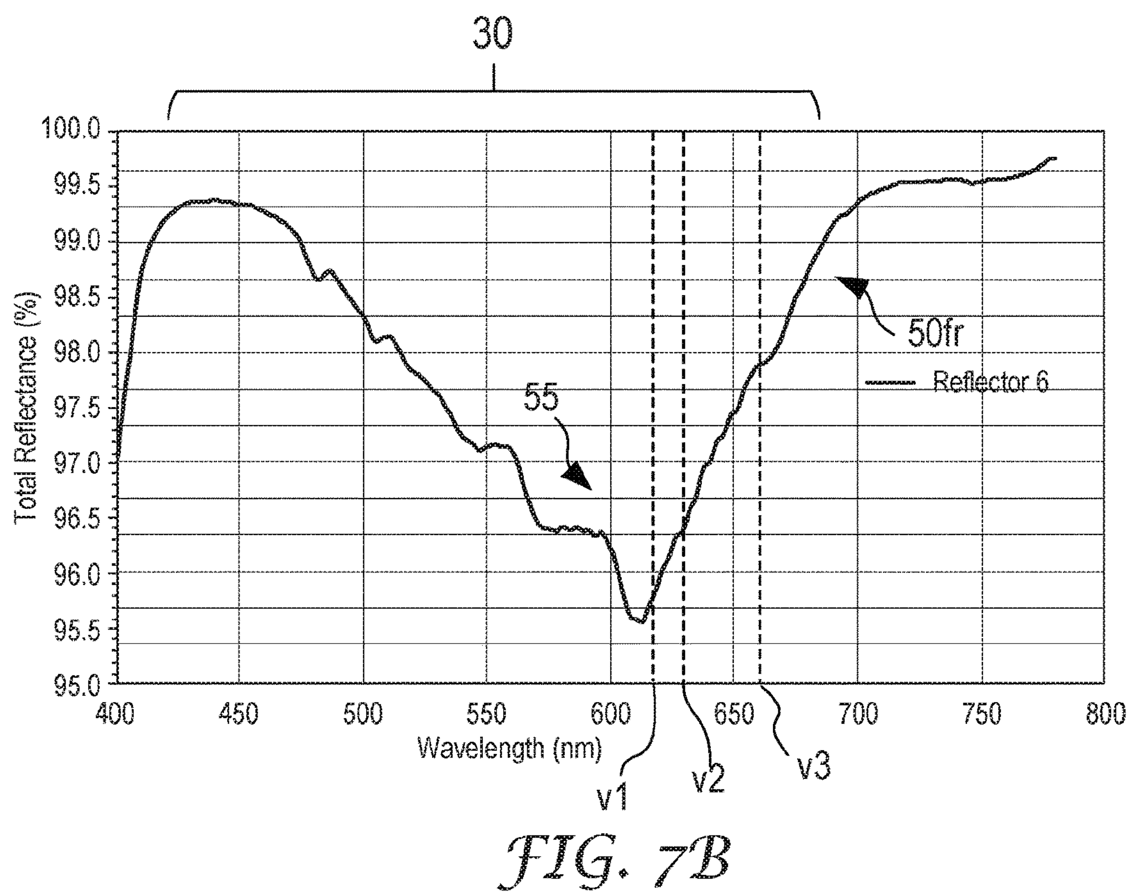

FIGS. 5 and 6A-6B show additional plots of percent optical transmission versus wavelength for optical reflector 50*f*, showing additional details for a range of visible wavelengths, according to the present description. FIGS. 7A-7B show plots of percent optical reflectance versus wavelength for an optical reflector in the visible wavelength range, according to the present description. Looking first at FIG. 5, showing plots of transmission versus wavelength for two different reflector types, 50*a* and 50*f*, each of the bandpass segments 51*a*, 51*f* exhibits a global peak 53*a*, 53*f* at a global peak wavelength 54*a*, 54*f* disposed in the visible wavelength range. In some embodiments, at least one visible wavelength (e.g., visible wavelength v3) is within about 50 nm, or about 40 nm, or about 30 nm, or about 20 nm of the global maximum 53*a*, 53*f* of the bandpass segment 51*a*, 51*f*.

FIGS. 6A and 6B provide a more detailed plot 50*f* of transmission versus wavelength for optical reflector 40 in the visible wavelength region, including bandpass region 51*f* and FWHM 52*f*. As seen in this plot, visible wavelength v3 at about 660 nm is included within the FWHM 52*f* and has a transmission percentage between 2.5% and 3.0%. FIGS. 7*a* and 7*b* provide a plot 50*fr* of optical reflectance percentage versus wavelength for the plurality of polymeric layers 41, 42 of optical reflector 40 for visible wavelength range 30. In some embodiments, plot 50*fr* may exhibit a region of lower reflectance 55 which includes one or more of visible wavelengths v1, v2, v3.

Figure 8A:
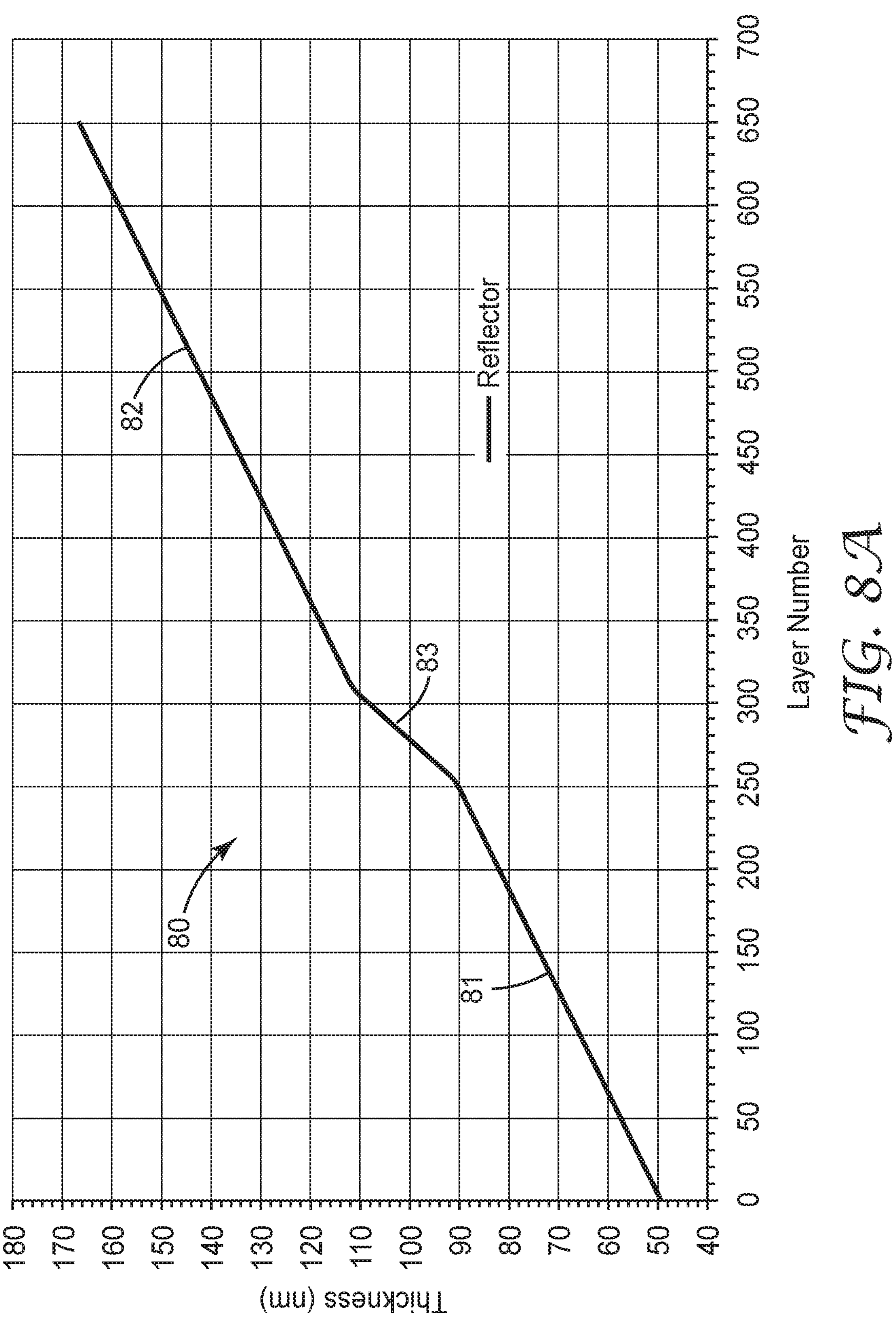
FIGS. 8A-8D are plots of a polymer layer thickness gradient and related slopes for an optical film, in accordance with an embodiment of the present description.
Figure 8C:
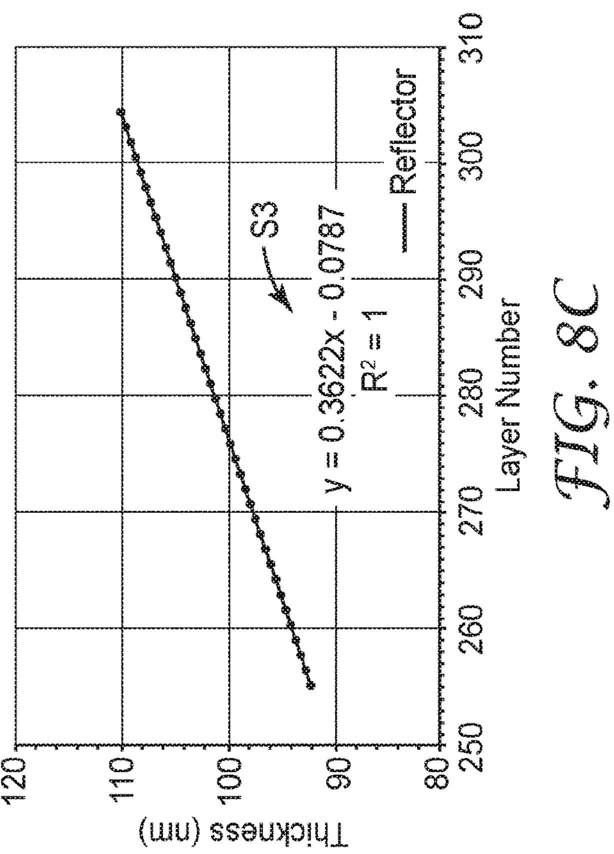
Figure 8B:
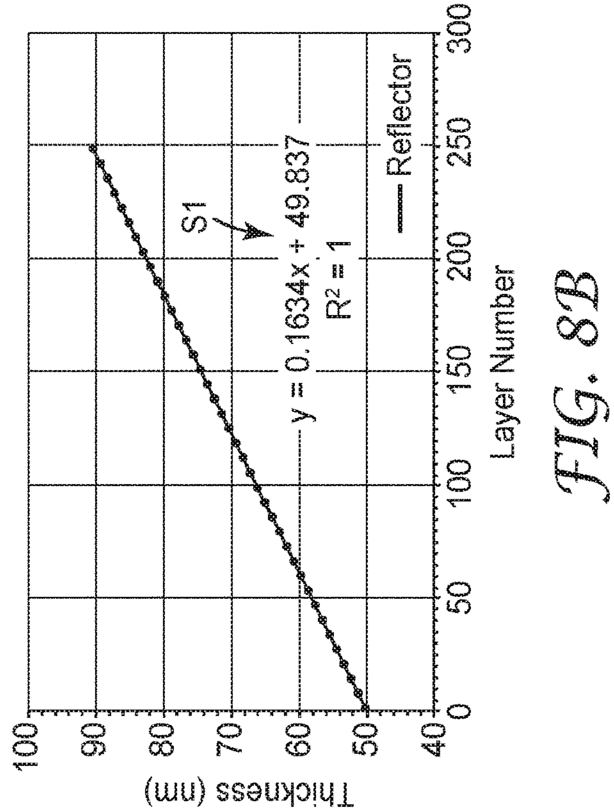
Figure 8D:
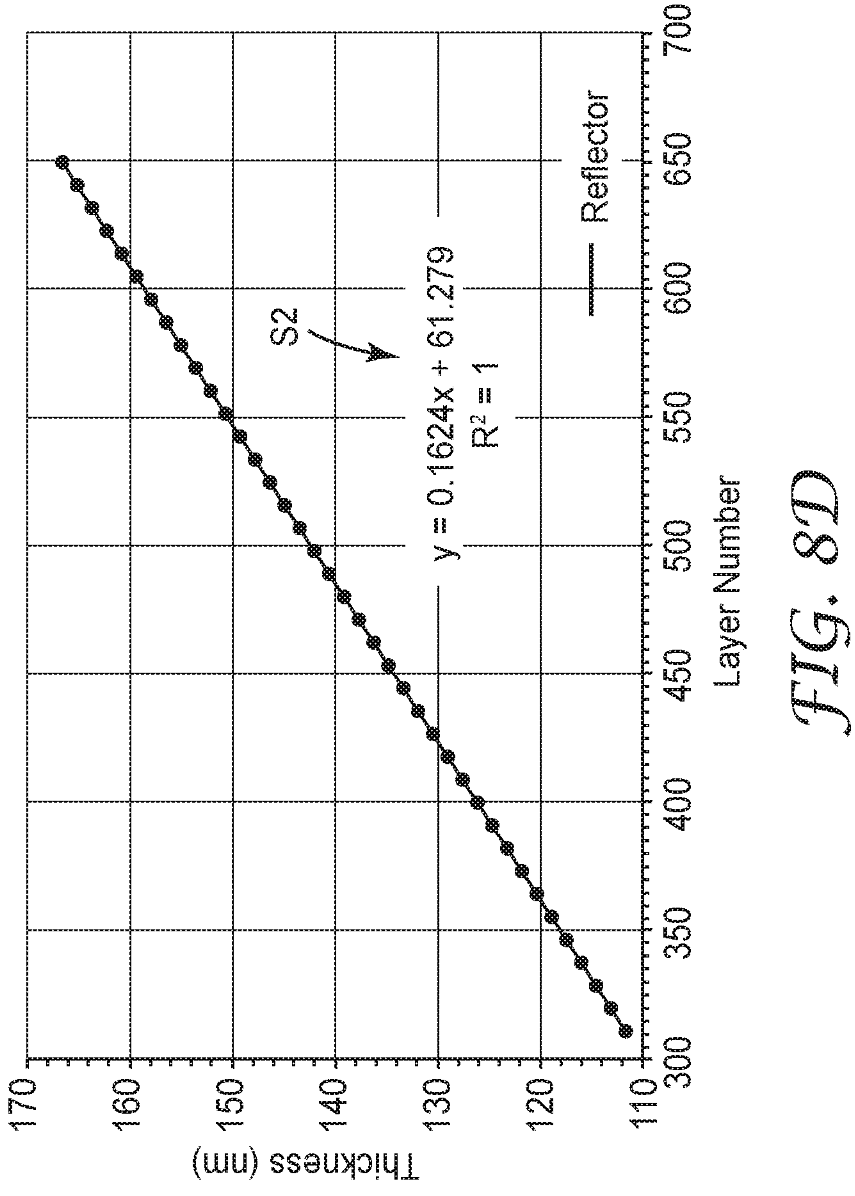

FIGS. 8A-8D are plots of a polymer layer thickness gradient and related slopes for an optical reflector 40 of FIGS. 1 and 2, according to the present description. FIG. 8A shows a polymer layer thickness gradient 80 for the plurality of polymeric layers 41, 42 (FIG. 2) of optical reflector 40 (FIGS. 1 and 2). In some embodiments, polymer layer thickness gradient 80 may include first substantially linear portion 81 and second substantially linear portion 82 joined by a third substantially linear portion 83. In some embodiments, each of the first 81 and second 82 portions may extend across at least 75, or at least 100, or at least 125, or at least 150, or at least 175, or at least 200, or at least 225, sequentially arranged polymeric layers in the plurality of polymeric layers. In some embodiments, the third linear portion 83 may extend across less than about 75 sequentially arranged polymeric layers in the plurality of polymeric layers 41, 42. FIGS. 8B, 8C, and 8D show plots of best linear fits to each of the first 81, second 82, and third 83 substantially linear portions, which exhibit respective linear slope magnitudes S1, S2 and S3. In some embodiments, S3 is greater than each of S1 and S2 by at least a factor of 1.5, or at least a factor of 1.6, or at least a factor of 1.7, or at least a factor of 1.8, or at least a factor of 1.9, or at least a factor of 2, or at least a factor of 2.1, or at least a factor of 2.2.

Figure 9:
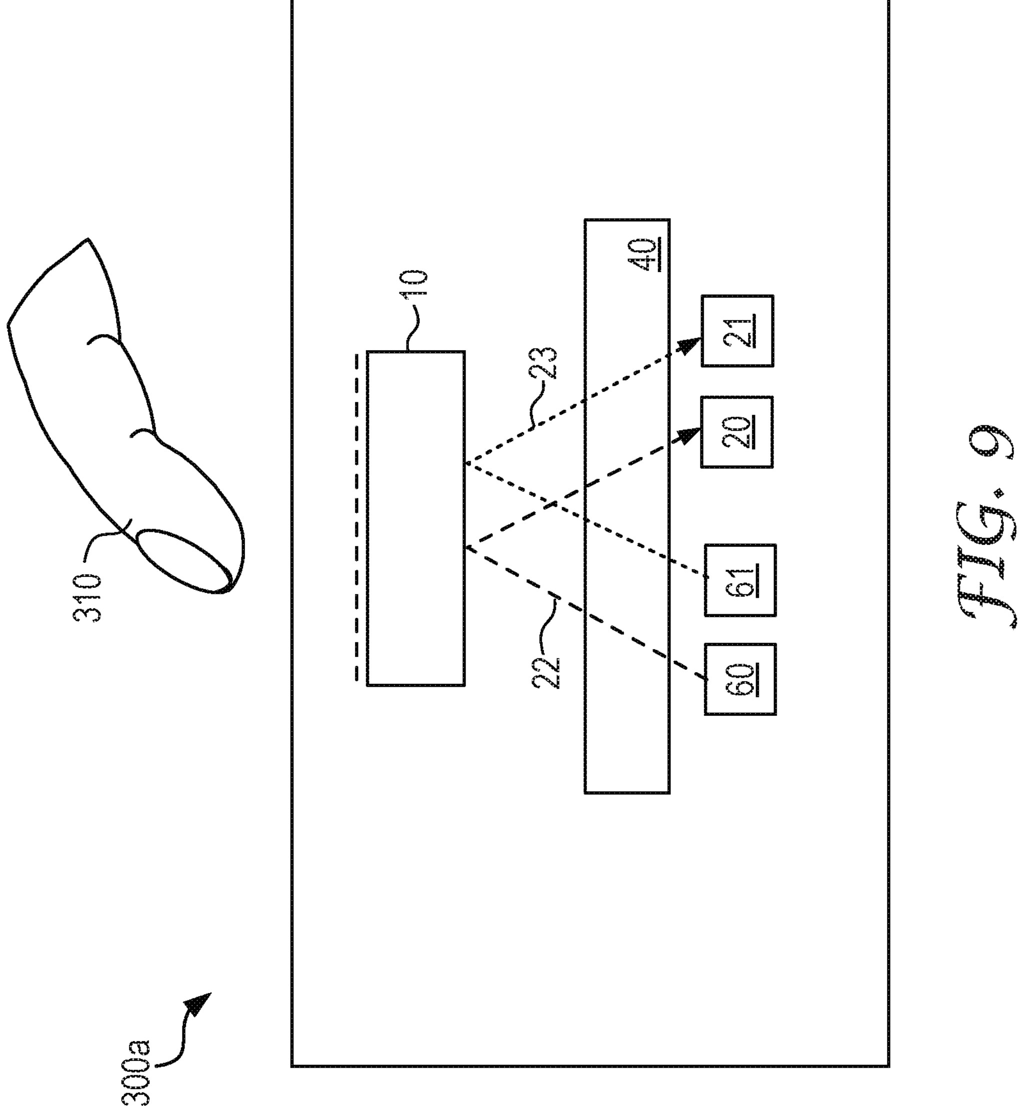
FIG. 9 shows an alternate embodiment of a display system for sensing a body portion of a user, in accordance with an embodiment of the present description.

FIG. 9 shows an alternate embodiment of a display system for sensing a body portion of a user, according to the present description. In display system 300*a*, the optical reflector 40 may be disposed between the display panel 10 and the at least one optical sensor 20, 21. In some embodiments, optical reflector 40 may also be disposed between display panel 10 and at least one light source 60, 61, which are configured to emit the visible light 22 and infrared light 23. In some embodiments, the emitted visible 22 and infrared lights 23 are sequentially transmitted by optical reflector 40, transmitted by display panel 10, reflected by a user body portion 310, transmitted again by display panel 10, transmitted again by optical reflector 40, and sensed by the at least one optical sensor 20, 21.

Figure 10:
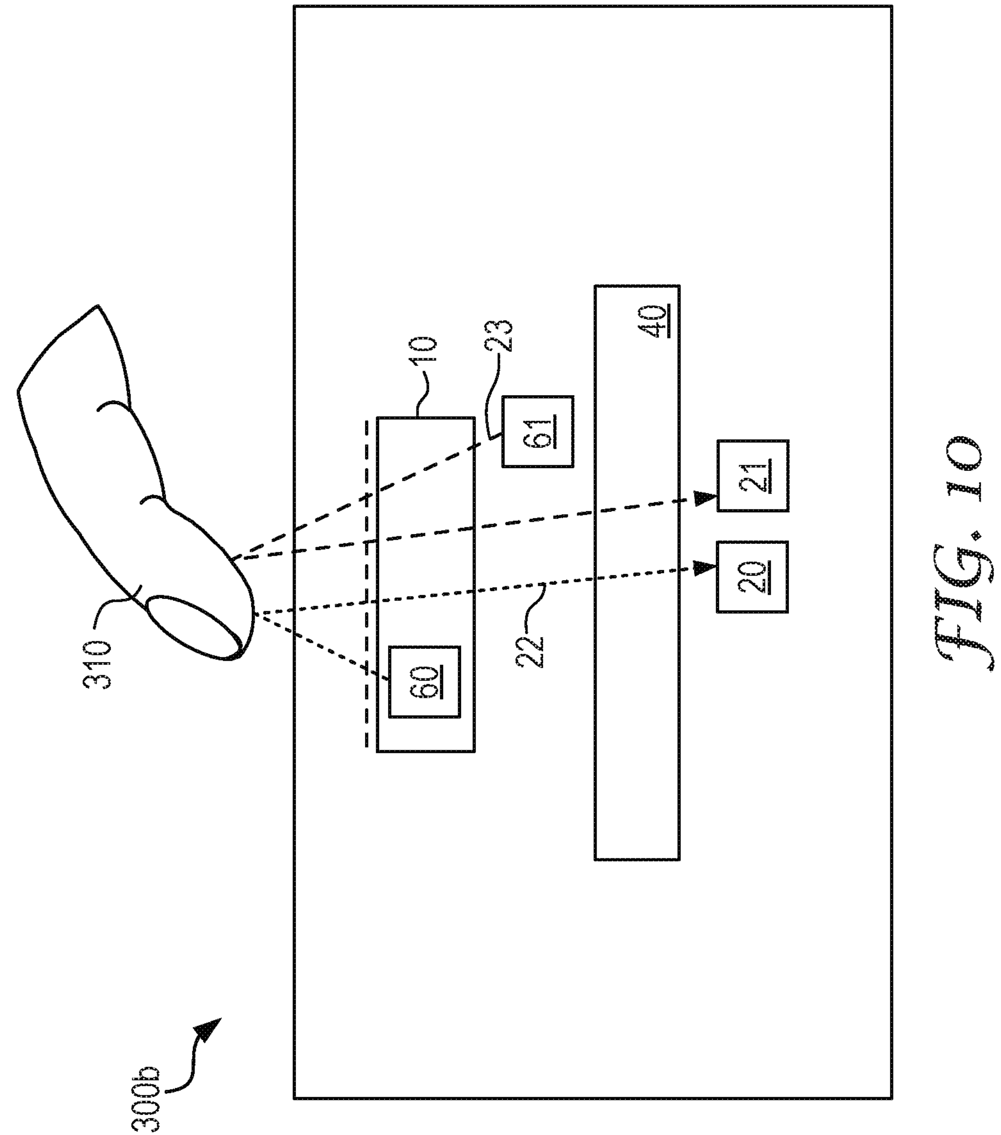
FIG. 10 shows another alternate embodiment of a display system for sensing a body portion of a user, in accordance with an embodiment of the present description.

FIG. 10 shows an alternate embodiment of a display system for sensing a body portion of a user, according to the present description. In some embodiments, display system 300*b* may include a visible-light light source 60 include in display panel 10 and configured to emit the visible light 22 and an infrared-light light source 61 disposed between display panel 10 and the optical reflector 40 and configured to emit infrared light 23. In some embodiments, the emitted visible light 22 may be sequentially reflected by the user body portion 310, transmitted by display panel 10, transmitted by the optical reflector 40, and sensed by visible-light optical sensor 20, and the emitted infrared light 23 may be sequentially transmitted by the display panel 10, reflected by the user body portion 310, transmitted again by the display panel 10, transmitted by the optical reflector 40, and sensed by infrared-light optical sensor 21.

Figure 11:
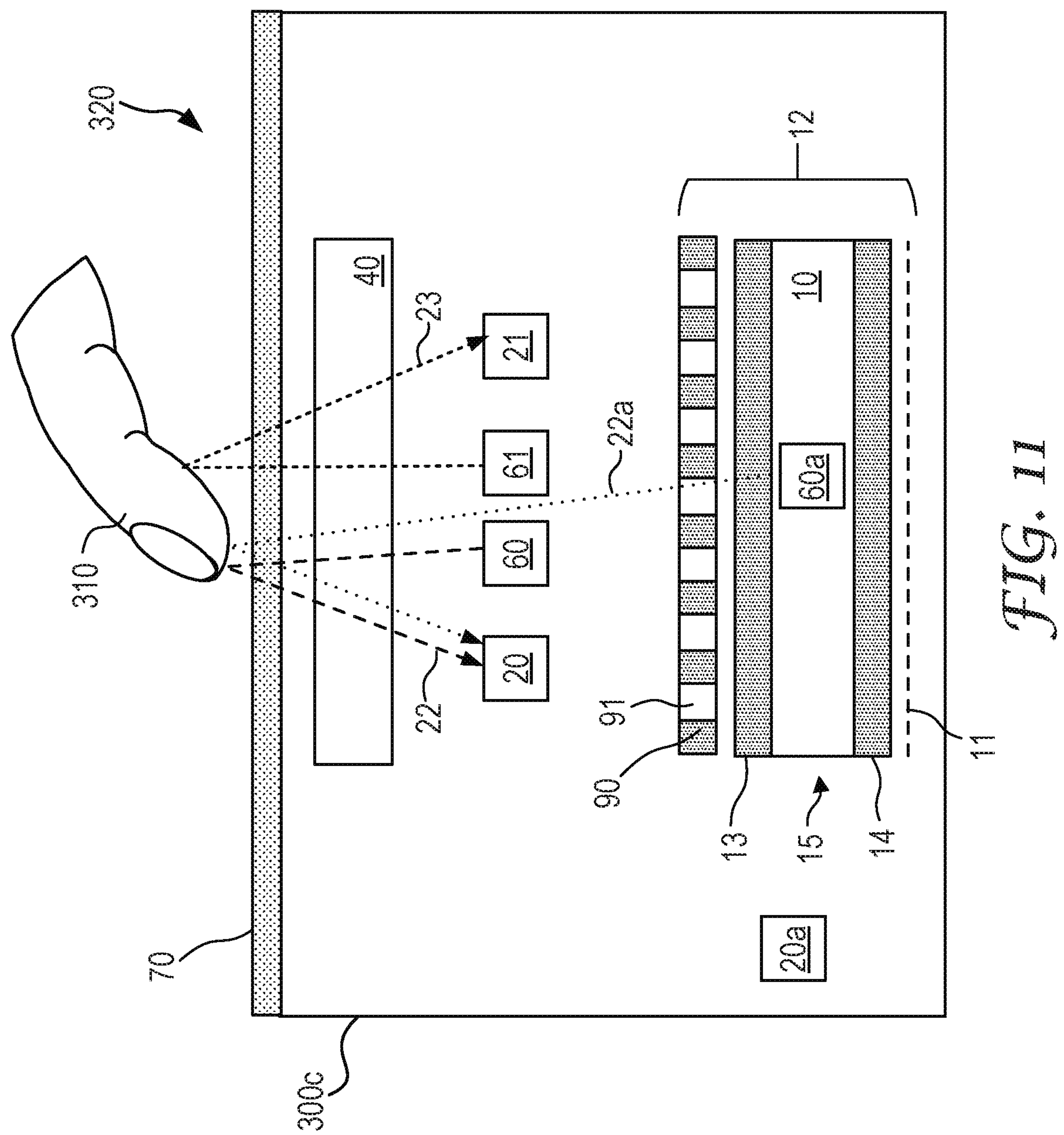
FIG. 11 shows another alternate embodiment of a display system for sensing a body portion of a user, in accordance with an embodiment of the present description.

Finally, FIG. 11 shows another alternate embodiment of a display system for sensing a body portion of a user, according to the present description. In some embodiments, display system 300*c* includes first optical reflector 40 and second optical reflector 90, a display 12, at least one optical sensor 20, 21, 20*a* and at least one light source 60, 61, 60*a*. In some embodiments, display 12 includes display panel 10 disposed between first polarizer 13 and second polarizer 14. In some embodiments, each of the optical reflector 40, 90 include a plurality of polymeric layers 41, 42 (see FIG. 2) numbering at least 50, or at least 100, or at least 250, or at least 300, or at least 400, or at least 500, or at least 600, in total. In some embodiments, each of the polymeric layers 41, 42 may have an average thickness of less than about 500 nm, or less than about 400 nm, or less than about 300 nm, or less than about 200 nm. In some embodiments, for a substantially normally incident light (see 43, FIG. 2), at least one visible wavelength (v1-v3, FIG. 4) in a visible wavelength range 30 extending from about 420 nm to about 680 nm, and at least one infrared wavelength (i1, i2, FIG. 3) in an infrared wavelength range (31) extending from about 750 to about 1500 nm, the plurality of polymeric layers 41, 42 of each of the optical reflectors 40, 90 may have an average optical reflectance of greater than about 80%, or greater than about 85%, or greater than about 90%, or greater than about 95%, in visible wavelength range 30, and an optical transmittance of greater than about 2%, or greater than about 2.5%, or greater than about 3%, or greater than about 3.5%, or greater than about 4%, or greater than about 10%, or greater than about 20%, or greater than about 30%, at the at least one visible wavelength v1, v2, v3. In some embodiments, the plurality of polymeric layers 41, 42 of the first optical reflector 40 may have an optical transmittance of greater than about 50%, or greater than about 60%, or greater than about 65%, or greater than about 70%, or greater than about 75%, or greater than about 80%, at the at least one infrared wavelength i1, i2. In some embodiments, the plurality of polymeric layers 41, 42 of the second optical reflector 90 may have an optical reflectance of greater than about 50%, or greater than about 60%, or greater than about 65%, or greater than about 70%, or greater than about 75%, or greater than about 80%, at the at least one infrared wavelength i1, i2.

In some embodiments, at least one of the at least one optical sensor 20, 21 may be disposed between optical reflector 40 and the display panel 10. In some embodiments, display system 300*c* may be configured to sense a user body portion 310 applied to a back side 320 of display system 300*c*, back side 320 being opposite the image 11 formed by display panel 10.

In some embodiments, display system 300*c* further includes a cover 70 disposed on back side 320 of display system 300*c*. In some embodiments, optical reflector 40 disposed between cover 70 and the at least one optical sensor 20, 21, 20*a*. In some embodiments, for a substantially normally incident light 43 (FIG. 2) and for each of the at least one visible wavelength v1, v2, v3 (FIG. 4) and the at least one infrared wavelength i1, i2 (FIG. 3), cover 70 may have an optical transmittance of greater than about 50%, or greater than about 60%, or greater than about 70%, or greater than about 80%.

In some embodiments, the visible-light light source 60 and infrared-light light source 61 may be disposed between optical reflector 40 and display panel 10. In some embodiments, visible-light light source 60 may be configured to emit visible light 22 having the at least one visible wavelength v1, v2, v3, and infrared-light light source 60 may be configured to emit infrared light 23 having the at least one infrared wavelength i1, i2, such that the emitted visible light 22 and infrared light 23 are sequentially transmitted by the optical reflector 40, reflected by the user body portion 310, transmitted again by the optical reflector 40, and sensed by the at least one optical sensor 20, 21.

In some embodiments, display 12 may include display panel 10 disposed between a first polarizer 13 and a second polarizer 14. In some embodiments of display system 300*c*, at least one of the first polarizer 13 and second polarizer 14 is an absorbing polarizer.

In some embodiments, second optical reflector 90, disposed between optical reflector 40 and the display panel 10, for a substantially normally incident light 43 (FIG. 2), may have an average optical reflectance of greater than about 80%, or greater than about 90%, or greater than about 95%, in the visible wavelength range 30 and an optical reflectance of greater than about 80%, or greater than about 90%, or greater than about 95%, at the at least one infrared wavelength i1, i2. In some embodiments, second optical reflector 90 may include at least one first segment 91 that has an optical transmittance of greater than about 5%, or greater than about 10%, or greater than about 20%, at the at least one visible wavelength v1, v2, v3. In some embodiments, the at least one first segment 91 is a physical through-opening in second optical reflector 90.

In some embodiments, the at least one optical sensor includes one or more visible-light optical detectors 20, 20*a* configured to sense the visible light 22 having the at least one visible wavelength v1, v2, v3. In some embodiments, visible-light optical detectors 20, 20*a* may comprise a first visible light detector 20 disposed between optical reflector 40 and display 10. In some embodiments, visible-light optical detectors 20, 20*a* may instead (or additionally) include a second visible-light detector 20*a* disposed on a lateral side 15 of the display 10. In some embodiments, display 10 may further include a visible-light light source 60*a*.

Terms such as "about" will be understood in the context in which they are used and described in the present description by one of ordinary skill in the art. If the use of "about" as applied to quantities expressing feature sizes, amounts, and physical properties is not otherwise clear to one of ordinary skill in the art in the context in which it is used and described in the present description, "about" will be understood to mean within 10 percent of the specified value. A quantity given as about a specified value can be precisely the specified value. For example, if it is not otherwise clear to one of ordinary skill in the art in the context in which it is used and described in the present description, a quantity having a value of about 1, means that the quantity has a value between 0.9 and 1.1, and that the value could be 1.

Terms such as "substantially" will be understood in the context in which they are used and described in the present description by one of ordinary skill in the art. If the use of "substantially equal" is not otherwise clear to one of ordinary skill in the art in the context in which it is used and described in the present description, "substantially equal" will mean about equal where about is as described above. If the use of "substantially parallel" is not otherwise clear to one of ordinary skill in the art in the context in which it is used and described in the present description, "substantially parallel" will mean within 30 degrees of parallel. Directions or surfaces described as substantially parallel to one another may, in some embodiments, be within 20 degrees, or within 10 degrees of parallel, or may be parallel or nominally parallel. If the use of "substantially aligned" is not otherwise clear to one of ordinary skill in the art in the context in which it is used and described in the present description, "substantially aligned" will mean aligned to within 20% of a width of the objects being aligned. Objects described as substantially aligned may, in some embodiments, be aligned to within 10% or to within 5% of a width of the objects being aligned.

All references, patents, and patent applications referenced in the foregoing are hereby incorporated herein by reference in their entirety in a consistent manner. In the event of inconsistencies or contradictions between portions of the incorporated references and this application, the information in the preceding description shall control.

Descriptions for elements in figures should be understood to apply equally to corresponding elements in other figures, unless indicated otherwise. Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

What is claimed is:

1. A display system for sensing a user body portion placed at or proximate to the display system, the display system comprising:

a display panel configured to form an image for viewing by the user;

an optical reflector comprising a plurality of polymeric layers numbering at least 50 in total, each of the polymeric layers having an average thickness of less than about 500 nm; and at least one optical sensor configured to sense a visible light having at least one visible wavelength in a visible wavelength range extending from about 420 nm to about 680 nm and an infrared light having at least one infrared wavelength in an infrared wavelength range extending from about 750 to about 1500 nm, the at least one optical sensor sensing the visible and infrared lights after the visible and infrared lights are transmitted by the optical reflector;

such that for a substantially normally incident light, the plurality of polymeric layers of the optical reflector has:

an average optical reflectance of greater than about 80% in the visible wavelength range;

an optical transmittance of greater than about 50% at the at least one infrared wavelength;

an optical transmittance of greater than about 2% and less than about 10% at the at least one visible wavelength; and an optical transmittance versus wavelength that comprises a bandpass segment comprising a full width at half maximum (FWHM) that comprises the at least one visible wavelength.

2. The display system of claim 1, wherein the user body portion comprises one or more of a finger of the user, a palm of the user, a vein of the user, a face of the user, and a vein pattern of the user.

3. The display system of claim 1, wherein the at least one optical sensor is configured to at least measure an intensity of at least one of the visible and infrared lights, and form a one- or a two-dimensional image of the user body portion.

4. The display system of claim 1, wherein the at least one optical sensor comprises a visible-light optical detector configured to sense the visible light having the at least one visible wavelength, and an infrared-light optical detector configured to sense the infrared light having the at least one infrared wavelength.

5. The display system of claim 1 further comprising at least one light source configured to emit the visible light having the at least one visible wavelength and the infrared light having the at least one infrared wavelength, such that the emitted visible and infrared lights are sensed by the at least one optical sensor after the emitted visible and infrared lights are first reflected by the user body portion and then transmitted by the optical reflector.

6. The display system of claim 5, wherein the at least one light source comprises a visible-light light source configured to emit the visible light having the at least one visible wavelength and an infrared-light light source configured to emit the infrared light having the at least one infrared wavelength.

7. The display system of claim 1, wherein the optical reflector is disposed between the display panel and the at least one optical sensor.

8. The display system of claim 7 further comprising at least one light source configured to emit the visible light having the at least one visible wavelength and the infrared light having the at least one infrared wavelength, the optical reflector disposed between the display panel and the at least one light source, such that the emitted visible and infrared lights are sequentially transmitted by the optical reflector, transmitted by the display panel, reflected by the user body portion, transmitted by the display panel, transmitted by the optical reflector, and sensed by the at least one optical sensor.

9. The display system of claim 7 further comprising a visible-light light source comprised by the display panel and configured to emit the visible light having the at least one visible wavelength and an infrared-light light source disposed between the display panel and the optical reflector and configured to emit the infrared light having the at least one infrared wavelength, such that the emitted visible light is sequentially reflected by the user body portion, transmitted by the display panel, transmitted by the optical reflector, and sensed by the at least one optical sensor, and the emitted infrared light is sequentially transmitted by the display panel, reflected by the user body portion, transmitted by the display panel, transmitted by the optical reflector, and sensed by the at least one optical sensor.

10. The display system of claim 1 further comprising a light redirecting layer disposed on the optical reflector for redirecting at least one of the visible and infrared lights from propagating along a first direction to a propagating along a different second direction.

11. The display system of claim 10, wherein the light redirecting layer comprises a plurality of prisms.

12. The display system of claim 1, wherein at least one of the at least one optical sensor is disposed between the optical reflector and the display panel.

* * * * *